United States Patent [19]

Hechemy

[11] 4,397,959

[45] Aug. 9, 1983

[54] FORCED PRECIPITATION METHOD FOR PREPARING ANTIGEN/ANTIBODY PARTICLES

[75] Inventor: Karim E. Hechemy, Clifton Park, N.Y.

[73] Assignee: Research Corporation, New York, N.Y.

[21] Appl. No.: 204,214

[22] Filed: Nov. 5, 1980

[51] Int. Cl.³ .................... G01N 33/48; G01N 33/54; C12Q 1/00; C12Q 1/04; C12Q 1/12; C12Q 1/10
[52] U.S. Cl. ........................ 436/509; 422/56; 422/57; 422/58; 435/7; 435/29; 435/34; 435/37; 435/38; 436/510; 436/513; 436/518; 436/531; 436/534; 436/547; 436/823; 436/826
[58] Field of Search .............. 424/3, 8, 12, 78, 79; 23/230 B; 435/7, 29, 34, 37, 38; 422/56, 57, 58; 436/509, 510, 513, 518, 531, 534, 547, 823, 826

[56] References Cited

U.S. PATENT DOCUMENTS 3,708,572  1/1973  Peetoom .................... 424/3 X

OTHER PUBLICATIONS

Levy, J., Immunol. Methods, vol. 22, 1978 pp. 131–142.
Makulu, Diabetes, vol. 18, No. 10, 1969, pp. 660–669.
Williams, Methods in Immunol. & Immunochem., Acd Press, NY, vol. IV, 1977, pp. 115–123.

Primary Examiner—Anna P. Fagelson
Attorney, Agent, or Firm—Scully, Scott, Murphy & Presser

[57] ABSTRACT

Process for the preparation of test reagents comprising antigens or antibodies adsorbed on a surface, for example, the surface of synthetic or natural polymer particles in which the test material to be adsorbed is dissolved in a solvent in contact with the adsorbing surface and precipitated by the addition of a liquid which is miscible with the solvent, but does not dissolve the test material.

20 Claims, No Drawings

FORCED PRECIPITATION METHOD FOR PREPARING ANTIGEN/ANTIBODY PARTICLES

This invention relates to the preparation of immunological reagents useful particularly for the determination of the presence of antibodies and antigens in mammalian fluids, such as human sera. The invention is particularly useful to test for the presence of infections in mammals including humans.

For convenience, the invention will be principally described as it relates to the immunodiagnosis of rickettsioses. Although, as will be seen, the techniques of the invention are applicable to detection of a variety of other infections.

Several tests are currently available for serological diagnosis of rickettsioses. The Weil-Felix test, developed in 1916, relies on a Proteus antigen. It is art recognized to be non-specific and to give rise to unacceptable percentages of false positive results with nonrickettsial disease and false negative results with clinically diagnosed cases of the rickettsial disease Rocky Mountain spotted fever. Hechemy et al, J. of Clin. Microbiol. 9:292 (1979).

Of the specific tests, the complement fixation test has been the test of choice. The test is cumbersome. Moreover, recent studies have pointed that the test lacks sensitivity. In one study, 86% of patients had false negative results in comparison with the microimmunofluorescence test. Hechemy et al, New England J. Med. 300:859 (1979) and Philip et al, Amer. J. Epid. 105:56 (1977).

Newer methodologies include the rickettsial microagglutination test which, though sensitive, requires large amounts of antigen. It has remained, primarily, a research tool. The microimmunofluorescence test, using *R. rickettsii* antigen has considerable value in rickettsial serology, but requires skilled technicians and expensive equipment. The indirect hemagglutination test, an overnight procedure, uses sensitized freshly prepared or glutaralydehyde stabilized red blood cells. Use of fresh erythrocytes adds 3 to 4 hours in reagent preparation time, and the stabilized cells have a shelf life of only 6 months.

Enzyme immunoassay and radioimmunoassay tests have been developed for certain rickettsia, e.g. *Rochalimaea quintana,* but these tests need further field evaluation to determine the extent of their utility as diagnostic tools.

Five rickettsial diseases are or have been endemic or epidemic in the United States: (1) Rocky Mountain spotted fever, caused by *Rickettsia rickettsii;* (2) rickettsial pox, caused by *R. akari;* (3) murine typhus, cased by *R. typhi;* (4) epidemic, louse borne typhus and Brill-Zinsser disease, caused by *R. prowazekii;* and Q fever, caused by *Coxiella burnetii.*

Rocky Mountain spotted fever is a significant health hazard in the United States. Since 1960, there has been a steady increase in the number of reported cases, particularly in the South Atlantic states.

This increasing caseload has given rise to an increasing demand for laboratory support. This demand coupled with the inadequacy of presently available tests as described above, has given rise to an acute need for a simple, rapid, sensitive, specific reproductible test for the presence of antirickettsial antibodies in mammalian sera. A technique has now been discovered which when used with specific antigens, for example solubilized antigen from *R. rickettsii* makes possible recognition of a wide variety of mammalian infections.

In immunodiagnosis using procedures in which antigens or antibodies have been adsorbed on a substrate, both man made and naturally occurring polymers have been used as carriers to detect antigen or antibodies. The ligands are attached to these vehicles by direct adsorption or by coupling. Although this immunoassay technique is simple, rapid and specific, its application has been restricted by the need for highly purified reagents. High purity is essential in direct adsorption because contaminants will compete for space on the adsorbing polymer particle. Large amounts of these highly purified components are required for chemical coupling to be successful. The need then, is to develop a test which avoids the necessity for large amounts of highly purified reagents.

Adsorption procedures are applicable to a wide variety of adsorption particles, e.g. charcoal, latex, pigments, bentonite, cellulose acetate and other well known materials. Typically useful latices include those derived from polystyrene, polyacrylates, polyvinyl chloride and the like. In general, the antigen, antibody or other immunogenic test material is adsorbed from solution and the resulting antigenic particle is exposed to the material to be tested, e.g. human sera. If the adsorbate is an antigen and the complementary antibody is present in the sera there will be a reaction with the production of a detectable product. Detection of a reaction product constitutes a positive test result. The problem which has limited the growth of the adsorption technique has been the problem of producing large amounts of high purity compositions containing solubilized antigen or other test material to be adsorbed.

The process of this invention avoids the twin necessities of high purity and high quantity by a forced adsorption technique which involves forced precipitation of test materials onto the surface of inert carriers. The method reduces the need for large quantities of highly purified ligand because all components are forced to precipitate onto the selected surface. A higher yield of attachment is obtained since the reaction is forced to completion. Therefore, large quantities are not needed, and high purity of ligands is not crucial. Surprisingly, the precipitation of impurities along with the solubilized test material does not interfere with the sensitivity or specificity of tests employing the precipitated and adsorbed test material.

The method is applicable to preparation of antigenic test reagents for the detection of antibodies from rickettsia such as *R. rickettsii, R. prowazeki, R. typhi,* and others. It is also applicable to the detection of other types of serologically detectable materials as:

1. detection of rheumatoid arthritis antibodies
2. detection of *E. coli* infections
3. detection of trichinosis antibodies
4. detection of toxoplasma antibodies
5. detection of chlamydial antibodies In accordance with the procedure of the invention, a solution, suitably an aqueous solution containing dissolved test material, e.g. a solubilized antigen is prepared in the presence of an adsorbent surface. The test material is then force precipitated onto the surface, and is adsorbed thereon, by the addition of a precipitating agent which is miscible with the solvent of the solution but does not dissolve the test material. The adsorbing surface may be the surface of any of the particles mentioned above, e.g. charcoal, latex, etc. The presently preferred adsorbent surfaces are the surfaces of inert synthetic polymer particles such as polystyrene, polyvinyl chloride or polyacrylates distributed in polymer latices. However, other surfaces are also useful. For example, the test material can be precipitated on the substantially flat surface of the container in which the aqueous solution is prepared or to which it is transferred. This container may be a glass or a synthetic polymer such as polycarbonate, polystyrene, polyester, or polyacrylate. In fact, a variety of materials to the surface of which antigens or antibodies will attach are known. The selection of a particular adsorbing surface does not presently appear to be critical. The improvement of the invention lies in the forced precipitation of test material onto the selected adsorbing surface. This procedure is especially useful when the technique of this invention is applied to the enzyme linked immunoadsorbent assay procedure.

Other useful substrates are polymeric membranes which are supported in the container and act as substantially flat adsorbing surfaces for the precipitated test material. These membranes are well known and are prepared from a number of synthetic polymers such as polystyrene, polycarbonate, or polyvinyl chloride.

One of the more significant aspects of the process of the invention is the selection of a precipitating agent which does not destroy the biological activity of the test material, e.g. the test antigen or antibody. Another is that if particles are used as the adsorbing surface, it should be possible to resuspend them once they have been precipitated. The presently preferred precipitating agents for use with aqueous solutions of the test material are water soluble alcohols, suitable lower alkanols such as methanol or ethanol together with water soluble alkali metal salts such as sodium or potassium salts, preferably lower carboxylic acid salts. The preferred precipitating reagents for use with aqueous compositions are mixtures of alcohols and salts containing from 0.2% to 0.7% salt, most preferably ethanol and sodium acetate.

The technique of the invention is not limited to precipitation and adsorption of antigens or antibodies from aqueous solutions. These test materials can also be force precipitated from solutions of test materials in organic solvents. Many combinations are possible. For example liquid antigens can be precipitated from chloroform or ether solutions by the addition of alcohol. Test materials in alcohol solution can be precipitated by the addition of trichloroacetic acid.

For a better understanding of this invention, it may be desirable at this point to clarify the meaning of some of the terms used in its description. As used in this specification the term:

Test material means the ligand which is adsorbed on the surface of the adsorbent substrate and reacts with the substance for which the test is designed. It may, for example, be a solubilized antigen from *Neisseria gonorrhoeae* or a solubilized antigen from *R. rickettsii*.

Antigenic particle is the product obtained by adsorption of the test material on a particle substrate.

Test reagent is the test material adsorbed on the surface of an adsorbing substrate which may be either a particle or a flat surface.

Test reagent composition is the test reagent in the presence of a carrier. For example, it may be the test reagent in the form of antigenic particles suspended in an aqueous carrier, usually a buffered carrier. It may also be the same aqueous carrier in a container to the surface of which the test material is adsorbed, or in which an adsorbent membrane with test material on its surface is supported.

The first step in the process of this invention is the preparation of a solution of the test material. For convenience, the technique of the invention will be principally described as applied to aqueous solutions of test materials. Water soluble antigens and antibodies of many infectious microorganisms are known and have been prepared. The procedures all result in the preparation of aqueous solutions of the test materials employed in this invention.

Processes for the preparation of water solutions of trichinosis antigens are described in Bozievich, Pub. Health Rep. 1938, 53:2130–2138; Witebsky et al, New York State J. Med. 1942, 42:431–435; Tompkins et al, J. Clin. Path. 1955, 25:206–213. Water solutions of toxoplasma antigen from *Toxoplasma gondii* are prepared following the procedure for the preparation of glycoprotein from erythocytes as described by Grimwood et al, Exper. Parasit, 1979, 48:282–286. Water soluble antigens of *Chlamydia trachomatis* are prepared by applying the method of Chang et al, J. Immunol. 1954, 71:8–15 to *C. trachomatis* cultivated as described by Sterling et al, J. of General Microbiol. 1977, 100:31–42 and purified by the procedure of Grimwood et al loc. cit. The preparation of water solutions of test material used for the preparation of latex-immunoglobulin employed for the detection of rheumatoid arthritis antibodies is discussed in detail below, as is the procedure for the preparation of immunogenic particles used to determine the presence of *Escherichia coli* infections.

The aqueous solution of test material may be used directly for the preparation of a test reagent in which the adsorbing substrate is the surface of a container or membrane. In this direct utilization of the aqueous solution of the test material, the solution is placed in the container, or in the container in which the selected membrane is supported. Addition of the precipitating agent results in precipitation of the test material and adsorption thereof on the adsorbing substrate to produce a test reagent.

The presently preferred test reagents are prepared by precipitating the test material on the surface of the particles of a latex, for example, a polystyrene or polyvinyl chloride latex. One suitable latex useful for the preparation of the working latex suspension is available from Difco Laboratories of Detroit, Mich. under their catalog number 3102-65. This suspension which is understood to be a polystyrene polymer suspended in water with the assistance of surfactants is initially diluted 1:2 by adding an equal volume of distilled water. The optical density (O.D.) of the 1:100 suspension is read at $\lambda 650$. If the optical density is above 0.3 the 1:2 suspension is too concentrated. If it is below 0.3, the 1:2 suspension is too dilute. The 1:2 suspension is then either diluted by the addition of distilled water or made more concentrated by the addition of stock suspension. A 1:100 aliquot of the resulting more dilute or more concentrated solution is prepared and the O.D. again determined. This procedure is continued until a 1:100 aliquot with an O.D. of $3.3\pm0.01$ is obtained. This adjusted 1:2 suspension or working suspension from which this final aliquot is prepared will have a particle concentration of about $3.7 \times 10^{10}$ particles per ml.

The working suspension prepared as above described is quite easily prepared and is convenient to use. It is not essential, however, that the working suspension have a particle concentration which is quite accurately known. As a practical matter, particle concentrations of from about $10^9$ to $10^{11}$ particles per ml are useful, but appreciable variations from this range can be tolerated. It has been observed that sensitivity is generally increased with decreasing O.D.

The working suspension is used to prepare the test reagent. One particularly useful procedure is as follows:

One volume of working latex suspension (e.g. 246 ml) is centrifuged at 5° C. for 30 minutes at 10,000 rpm in a Sorvall centrifuge using an HB4 rotor. The supernatant is decanted, saved and kept at 5° C. For convenience, it is labeled as Supernatant A.

The latex is suspended in 10-20 ml of 0.1 M glycine buffered 0.85% saline (GBS:pH 8.2) at room temperature.

The appropriate volume of antigen as determined by checkerboard titration is then added at room temperature, e.g. 21 ml of solubilized antigen solution prepared as described by Anacker et al, Infection And Immunity, Vol. II, No. 6, 1203-1209 (1975) by boiling 21 mg of *R. rickettsii* organisms in 21 ml of 0.2 N sodium hydroxide aqueous saline solution for 30 minutes and dialyzing against Chang's buffer. The procedure is described in more detail below.

The mixture is stirred on a magnetic stirrer for about 15 minutes to break all clumps.

To the measured volume of mixture are added 10 volumes of 95% ethanol containing 0.5% by weight sodium acetate with continued stirring at room temperature.

Stirring is continued for an additional 30 minutes at room temperature and the mixture is left standing at about 5° C. to 10° C. for about 12 to 24 hours.

Centrifuge in a Sorvall centrifuge with an HB4 rotor at about 5° C. and about 10,000 rpm for 30 minutes, and decant and discard the supernatant.

Resuspend the antigenic particles in the retained Supernatant A and stir at room temperature until the clumps are broken and a fine suspension is obtained.

Continue stirring while adding 246 ml of GBS (the volume of GBS added is equal to the volume of the working latex suspension).

For every 100 ml of the thus prepared solution, add 12.5 ml of GBS containing 0.1% bovine albumin-fatty acid free (GBS-0.1% BAF).

This is one embodiment of the test reagent compositions of this invention. It comprises antigenic particles suspended in a buffered aqueous medium. The concentration of antigenic particles is about $1.7 \times 10^{10}$ particles per ml.

The GBS-0.1% BAF assists in stabilizing the suspension, but it is not essential to the preparation of useful test reagent compositions. It can be replaced with GBS or an equivalent buffer.

There are a number of variations of the exact procedure described above which can be employed for the preparation of test reagent compositions of the invention.

The reason for retaining the Supernatant A and reusing it is to take advantage of the surfactants in the original latex. These surfactants for suspending latex particles are known, and these can be utilized to suspend the antigenic particles of this invention. Thus, the retention of the original supernatant is not essential to the practice of the invention. The antigenic particles which precipitate upon the addition of the alcohol-salt mixture may be suspended in another aqueous mixture containing other surfactants, or the same surfactants.

It has been observed in working with ordinary latex working suspensions that better results were obtained when the suspension is incubated with sera to be tested, if the working suspension contains in addition to the ordinary antigenic particles with adsorbed antigen or antibody, a supplementary amount of the same solubilized antigen or antibody as a solute. The same is true with the improved antigenic particles of this invention. In order to prepare test reagent compositions of this invention which contain both free and bound antigens or antibodies, the foregoing specifically described procedure is varied as follows after 16 ml of solubilized antigen composition have been force precipitated by the addition of alcohol-salt mixture to produce antigenic particles which are separated by centrifugation and decantation of the supernatant:

Resuspend the antigenic particles in 20 ml of Supernatant A. Stir at room temperature until all clumps are broken and a fine suspension is obtained.

Add, while stirring at room temperature, approximately 5 ml of supplementary soluble antigen.

After the addition of the supplementary soluble antigen, continue stirring at room temperature for an additional 30 minutes.

Add the remaining volume of Supernatant A.

While stirring, gradually add about 241 ml of GBS so that the volume of supplementary soluble antigen and GBS added equals the original volume of the working latex suspension. Then, for every 100 ml of latex suspension plus supplementary soluble antigen plus GBS mixture, add 12.5 ml of GBS-0.1% BAF.

Two typical test reagent compositions containing antigenic particles at a concentration of about $3 \times 10^7$ particles per ml were prepared to contain the components shown in Table 1.

TABLE 1

| | 1 | 2 |
|---|---|---|
| SUPERNATANT A | 20 ml | 246 ml |
| SUPPL. SOLUBLE ANTIGEN | 5 ml | — |
| REMAINING SUPERNATANT A | 226 ml | — |
| GBS | 241 ml | 246 ml |
| GBS-0.1% BAF | 61.3 ml | 61.3 ml |
| TOTAL | 553.3 ml | 553.3 ml |

The amount of GBS-0.1% BAF added may vary from about 12 to 15 ml so that it forms about 12% to 15% by volume of the test reagent composition.

These reagent test compositions are preferably sonicated before use to aid in suspending the antigenic particles. Soluble or solubilized rickettsiae antigens may be prepared from rickettsiae strains grown on yolk sac or L-cells. The antigen may be purified by ether extraction, and further purified, if desired, by sucrose gradient. It is digested with sodium hydroxide and the resulting composition is dialyzed against isotonic phosphate-saline solution (Chang's buffer) as described in Chang et al, J. Immunol. 73, 8–15 (1954); Anacker et al, Can. J. Microbiol. 20, 1523–1527 (1974) and Anacker et al, Infection And Immunity 11, 1203–1209 (1975).

The procedure for preparing the rickettsiae microorganisms from either yolk sacs or infected L-cell pellets is described in the first two articles. The last article describes the procedure for preparing solubilized antigen. For the preparation of solubilized antigen, the gradient purified lyophilized rickettsiae are suspended in saline (1 mg/ml) and the suspension made 0.2 N with sodium hydroxide, digested by boiling for 30 minutes and then dialyzed against Chang's buffer. The solubilized antigen is in the retentate.

In the dialysis procedure, the boiled digestion medium is dialyzed for 24 hours at 3° C. to 8° C. against several changes of the buffer. The composition of Chang's buffer is:

| | |
|---|---|
| $Na_2HPO_4$ | 0.81 g |
| $KH_2PO_4$ | 1.04 g |
| NaCl | 6.8 g |
| Distilled $H_2O$ | 1000 ml |
| pH | 6.8 |

The following non-limiting examples illustrate the preparation of a variety of antigenic particles of this invention.

EXAMPLE 1

Antigenic Particles for Detection of Rheumatoid Arthritis Antibodies

Antigen Source: Fraction II globulin (Commercial source: Sigma Chemical Company HG II-Lot #79C-0199)

A. Preparation of Latex-Fraction II

Dissolve the Fraction II globulin (1 mg/ml) at room temperature in GBS pH 8.2.

Centrifuge 0.6 ml aliquots of the working latex suspension as prepared as described above in a Sorvall Centrifuge using an HB4 head at 10,000 rpms for 30 min. at 5° C. The supernatant is decanted, saved, and kept at 5° C. It is labeled Supernatant A.

Use checkerboard titration to determine the optimum concentration of Fraction II globulin needed for maximum serologic activity, and add the appropriate volume of Fraction II dissolved in GBS.

Stir the mixture on a magnetic stirrer for 15 min. until all clumps are broken.

To the volume of the mixture, add 10 volumes of ethanol-acetate mixture (95% ethanol containing 0.5% sodium acetate) while stirring at room temperature. Stir an additional 30 min. at room temperature. Leave approximately 18 hrs. at 5° C.

Centrifuge in a Sorvall Centrifuge with an HB4 rotor at 5° C. at 10,000 rpms for 30 min.

Decant and discard the supernatant.

Resuspend the antigenic particles in 0.2 ml of Supernatant A. Stir at room temperature until all clumps are broken and a fine suspension is obtained.

Add, while stirring at room temperature, additional Fraction II globulin in GBS so that there is approximately a 1:4 ratio of soluble antigen to latex bound antigen.

After the addition of the supplementary soluble antigen, continue stirring at room temperature for an additional 30 min.

Add the remaining volume of Supernatant A (0.4 ml). While stirring, gradually add GBS so that the volume of GBS and supplementary soluble antigen added equals the original volume of the working latex suspension.

Then, for every 0.6 ml of latex+antigen+GBS mixture, add 0.075 ml (12.5%) of GBS containing 0.1% Bovine albumin-fatty acid-free (GBS 0.1% BAF).

Sonicate for 15–30 seconds.

EXAMPLE 2

Antigenic Particle for Detection of Escherichia Coli Infections

A. Preparation of *Escherichia coli* 0111:B4 Soluble Antigen by EDTA Treatment

*Escherichia coli* 0111:B4 is grown for approximately 16 hours in beef heart infusion broth+0.1% glucose at 37° C. in 9 liter bottles containing 7 liters of broth with stirring.

Centrifuge at 14,000 rpms using a Sorvall continuous flow centrifuge. The cells are washed 3 times with 0.12 M Tris-Cl buffer, pH 8.0 and centrifuged using 500 ml (4) centrifuge bottles at 6,000 rpms for 25 minutes.

The pellets are weighed and homogenized in 0.12 M Tris buffer, pH 8.0 (0.2 g wet weight/ml).

To a prewarmed suspension at 37° C. EDTA is added at a final concentration of 0.01 M EDTA (added 1/10 volume of EDTA 0.1 M per volume of cells) and the EDTA treatment suspension incubated at 37° C. for 10 minutes with gentle shaking.

The reaction is terminated by adding 1/10 volume of $MgCl_2$ to a final concentration of 0.05 M.

Cells are then centrifuged at 6,000 rpms for 30 minutes in 500 ml bottles and the supernate filtered through 0.45 μm Millipore filters. The filtrate is dialyzed in distilled water with continuous changes until testing with 0.1% $AgNO_3$ showed no Cl ions.

The solution is then lyophilized.

B. Preparation of Latex-*Escherichia coli* lipopolysaccharide

Dissolve the *Escherichia coli* lipoplysaccharide (1 mg/ml) at room temperature in GBS pH 8.2.

Centrifuge 0.6 ml aliquots of the working latex suspension in a Sorvall Centrifuge using HB4 head at 10,000 rpms for 30 min. at 5° C.

The supernatatant is decanted, saved, and kept at 5° C. It is labeled Supernatant A.

Use checkerboard titration to determine the optimum concentration of *E. coli* lipopolysaccharide needed for maximum serologic activity, add appropriate volume of the *E. coli* lipopolysaccharide in GBS.

Stir the mixture on a magnetic stirrer (or vortex) for 15 min. until all clumps are broken.

To the volume of the mixture, add 10 volumes of ethanol-acetate mixture (95% ethanol containing 0.5% sodium acetate) while stirring at room temperature.

Stir an additional 30 min. at room temperature.

Leave approximately 18 hrs. at 5° C.

Centrifuge in a Sorvall Centrifuge with an HB4 rotor at 5° C. at 10,000 rpms for 30 min.

Decant and discard the supernatant.

Resuspend the antigenic particles in 0.2 ml of Supernatant A. Stir at room temperature until all clumps are broken and a fine suspension is obtained.

Add, while stirring at room temperature additional *E. coli* lipopolysaccharide in GBS so that there is approximately a 1:4 ratio of soluble lipopolysaccharide to latex bound antigen.

After the addition of the supplementary soluble polysaccharide, keep stirring at room temperature for an additional 30 min.

Add the remaining volume of Supernatant A (0.4 ml). While stirring, gradually add GBS so that the volume of GBS and supplementary soluble lipopolysaccharide added equals the original volume of the latex suspension.

Then, for every 0.6 ml of the latex+lipopolysaccharide+GBS mixture, add 0.075 ml (12.5%) of GBS containing 0.1% GBS-0.1% BAF.

Sonicate for 15 to 30 seconds.

EXAMPLE 3

Antigenic Particles for Detection of Trichinosis Antibodies

A. Preparation of Trichinosis Antigen from Trichinella larvae

The process is described in:

J. Bozicevich. Public Health Rep. 1938, 53:2130-2138, E. Witebsky, P. Wels, and A. Heide, New York State J. Med. 1942, 42:431-435, and V. N. Tompkins and T. F. Muraschi, Amer. J. Clin. Path. 1955, 25:206-213.

B. Preparation of Latex-Trichinosis

Centrifuge 0.6 ml aliquots of the working latex suspension in a Sorvall Centrifuge using HB4 head at 10,000 rpms for 30 min. at 5° C.

The supernatant is decanted, saved, and kept at 5° C. It is labeled Supernatant A.

Use the checkerboard titration to determine the optimum concentration of trichinosis antigen needed for maximum serologic activity, and add the approximate volume of the trichinosis antigen in aqueous buffer.

Stir the mixture on a magnetic stirrer for 15 min. until all clumps are broken.

To the volume of the mixture, add 10 volumes of ethanol-acetate mixture (95% ethanol containing 0.5% sodium acetate) while stirring at room temperature.

Stir an additional 30 min. at room temperature.

Leave approximately 18 hrs. at 5° C.

Centrifuge in a Sorvall Centrifuge with an HB4 rotor at 5° C. at 10,000 rpms for 30 min.

Decant and discard the supernatant.

Resuspend the antigenic particles in 0.2 ml of Supernatant A. Stir at room temperature until all clumps are broken and a fine suspension is obtained.

Add, while stirring at room temperature, supplementary soluble trichinosis antigen. There is approximately 1:4 ratio of soluble antigen to latex bound antigen. After the addition of the supplementary soluble antigen, keep stirring at room temperature for an additional 30 min.

Add the remaining volume of Supernatant A.

While stirring, gradually add triethenolamine buffered saline (TBS) so that the volume of TBS and supplementary soluble antigen added equals the original volume of the latex suspension.

Then, for every 100 ml of the latex+antigen+TBS mixture, add 12.5 ml (12.5%) of TBS containing 0.1% Bovine albumin-fatty acid-free (TBS-0.1% BAF).

Sonicate for 15 to 30 seconds.

EXAMPLE 4

Antigenic Particles for Detection of *Toxoplasma Gondii* Antibodies

A. Preparation of *Toxoplasma gondii* antigen

The cultivation and purification of the whole organism is described in:

Grimwood, B. G., K. Hechemy, and R. W. Stevens, Exper. Parasit. 1979, 48:282-286.

Preparation of the solubilized antigen is in accordance with the procedure used for the preparation of glycoprotein from erythrocytes as described in:

Fletcher, M. A., T. M. Lo, and W. R. Graves, J. Immol. 1976, 117:717-721.

B. Preparation of Latex-*Toxoplasma gondii*

Dissolve the *Toxoplasma gondii* (1 mg/ml) at room temperature in GBS pH 8.2.

Centrifuge 0.6 ml aliquots of the working latex suspension in a Sovall Centrifuge using a HB4 head at 10,000 rpms for 30 min. at 5° C.

The supernatant is decanted, saved, and kept at 5° C. It is labeled Supernatant A.

Use checkerboard titration to determine the optimum concentration of *Toxoplasma gondii* needed for maximum serologic activity and add approximate volume of the *T. gondii* in GBS.

Stir the mixture on a magnetic stirrer for 15 min. until all clumps are broken.

To the volume of the mixture, add 10 volumes of ethanol-acetate mixture (95% ethanol containing 0.5% sodium acetate) while stirring at room temperature.

Stir an additional 30 min. at room temperature.

Leave approximately 18 hrs. at 5° C.

Centrifuge in a Sorvall Centrifuge with an HB4 rotor at 5° C. at 10,000 rpms for 30 min.

Decant and discard the supernatant.

Resuspend the antigenic particles in 0.2 ml of Supernatant A.

Stir at room temperature, add supplementary soluble T. gondii antigen in GBS. There is approximately a 1:4 ratio of soluble antigen to latex bound antigen.

After the addition of the supplementary soluble antigen, keep stirring at room temperature for an additional 30 min. Add the remaining volume of Supernatant A (0.4 ml).

While stirring, gradually add GBS so that the volume of GBS and supplementary soluble antigen added equals the original volume of the latex suspension.

Then, for every 0.6 ml of the latex+antigen+GBS mixture, added 0.075 ml (12.5%) of GBS containing GBS-0.1% BAF.

Sonicate for 15 to 30 seconds.

EXAMPLE 5

Antigenic Particle for Detection of *Chylamydia Trachomatis* Antibodies

A. Preparation of *Chylamydia trachomatis* antigen

The cultivation of the *Chlamydia trachomatis* follows the method described in:

Stirling, P. and S. Richmond, J. of General Microbiol. 1977, 100:31-42.

The purification of the microorganism follows the procedure described in:

Grimwood, B. G., K. Hechemy, and R. W. Stevens, Exper. Parasit. 1979, 48:282-286.

The solubilized antigen is prepared by the Chang procedure as described above for the preparation of solubilized antigen from *R. rickettsii.*

B. Preparation of Latex-*Chlamydia trachomastis*

Centrifuge 0.6 ml aliquots of the working latex suspension in a Sorvall Centrifuge using an HB4 head at 10,000 rpms for 30 min. at 5° C.

The supernatant is decanted, saved, and kept at 5° C. It is labeled Supernatant A.

Use checkerboard titration to determine the optimum concentration of solubilized *C. trachomatis* needed for maximum serologic activity. And add approximate volume of the *C. trachomastis* in GBS.

Stir the mixture on a magnetic stirrer for 15 min. until all clumps are broken.

To the volume of the mixture, add 10 volumes of ethanol-acetate mixture (95% ethanol containing 0.5% sodium acetate) while stirring at room temperature.

Stir an additional 30 min. at room temperature.

Leave approximately 18 hrs. at 5° C.

Centrifuge in a Sorvall Centrifuge with an HB4 rotor at 5° C. at 10,000 rpms for 30 min.

Decant and discard the supernatant.

Resuspend the antigenic particles in the retained Supernatant A.

Stir at room temperature until all clumps are broken and a fine suspension is obtained, for an additional 30 min.

While stirring, gradually add GBS containing 0.1% GBS-0.1% BAF.

Sonicate for 15 to 30 seconds.

The forced adsorption technique of this invention is applicable to the detection of infectious mononucleosis in humans. To apply the technique, a glycoprotein solubilized antigen from ox cell membrane is force precipitated as described above and the resulting antigenic particles incubated with sera from the suspected patient.

The test reagent compositions of the invention are used to test mammalian sera for the presence of antigens or antibodies indicative of an infection. They can, for example, be employed to test human sera for the presence of R. rickettsii antibodies. The procedure is as follows:

The serum to be tested is diluted to 1:16 in GBS-0.1% BAF and heated for 30 min. at 56° C. in a water bath to destroy complement and reduce non-specific activity. To 0.040 ml of the test serum there is added 0.020 ml of the test reagent composition. The components are mixed by stirring and rotated by hand or on a VDRL platform shaker for 6 min. and left to rest in a humidity chamber for 5 min. If aggregation is observed, the test serum is serially diluted and the reciprocal of the highest dilution where a definite aggregation is observed, is considered to be the titer.

To determine the threshold value of the reactivity of the forced adsorptions latex-R. rickettsii test, 124 single specimens and the second specimens of 118 pairs were grouped according to their micro-IF/Ig titers into reactive (≧128), weakly reactive (64), and non reactive (<64), and their distribution was plotted according to the latex-*R. rickettsii* titer.

For single sera there were no micro-IF/Ig reactives with latex-*R. rickettsii* titers ≦16. At a latex-*R. rickettsii* titer of 32 three sera were nonreactive; two others, also micro-IF/Ig-nonreactive, were scored reactive because they had micro-IF/IgM titers of 32; and one serum was weakly reactive. The latex-*R. rickettsii* titer of 64 was the lowest at which most sera were reactive by micro-IF. Five of the eight were reactive, two because they had micro-IF/IgM titers of 32; two other sera were weakly reactive, and one was nonreactive. At latex-*R. rickettsii* titers ≧128 vitually all sera were reactive.

For the second sera of paired sera, at a latex-*R. rickettsii* titer of ≦16, 28 were nonreactive, and 1 was weakly reactive by micro-IF. However, the first specimen of one of these pairs had high titers by latex-*R. rickettsii,* IHA, micro-IF, and CF.

At a latex-*R. rickettsii* titer of 32, half of the 10 sera were nonreactive. The first specimens of these 5 pairs had latex-*R. rickettsii* titers of 16 to 64; thus there was not a fourfold rise in titer. The other 5 sera were reactive. The first specimens of these pairs had latex-*R. rickettsii* titers <16; thus a fourfold rise in titer would have been observed, and the second specimen would have been reported as reactive.

At a latex-*R. rickettsii* titer of ≧64 all second sera were reactive by micro-IF.

By this procedure the following threshold values of reactivity for the latex-*R. rickettsii* test were established: for single specimens, a titer of 64; for paired sera, an individual titer of 64 of a fourfold rise in titer to ≧32. A single titer of 32 was considered weakly reactive.

These procedures were used to evaluate the forced adsorption technique as applied to the slide latex agglutination test for *R. rickettsii* antibodies using the micro-IF test as a standard. Sera from 2656 patients were tested by both the latex test and the micro-IF test with the results shown in Table 2.

TABLE 2

Comparison of Latex-*Rickettsi rickettsii* with Micro-IF Results

| Latex-*R. rickettsii* Results | Micro-IF results Reactive | Weakly and nonreactive | No. of Patients |
|---|---|---|---|
| Reactive | 379 | 29 | 408 |
| Weakly and nonreactive | 25 | 2223 | 2248 |
| No. of patients | 404 | 2252 | 2656 |

Relative to the Micro-IF test:

Specificity = 98.72%
Sensitivity = 93.81%

Predictive value of
negative result = 98.88%
positive result = 92.89%
Efficiency = 97.96%

The various values in Table 2 are calculated as follows:

$$\text{Specificity} = \frac{\text{Latex nonreactive results}}{\text{Micro-}IF\text{ nonreacitve results}} \times 100 = \frac{2223}{2252} \times 100 = 98.72\%$$

$$\text{Sensitivity} = \frac{\text{Latex reactive results}}{\text{Micro-}IF\text{ reactive results}} \times 100 = \frac{379}{404} \times 100 = 93.81\%$$

$$\text{Predictive Value of Negative Result} = \frac{\text{True negative results}}{\text{True negative \& False negative results}} \times 100 = \frac{2223}{2223 + 25} = 98.88\%$$

$$\text{Predictive Value of Positive Result} = \frac{\text{True positive results}}{\text{True positive \& False positive results}} \times 100 = \frac{379}{379 + 29} = 92.89\%$$

$$\text{Efficiency} = \frac{\text{True positive and negative results}}{\text{Total results}} \times 100 = \frac{379 + 2223}{379 + 2223 + 29 + 25} \times 100 = 97.96\%$$

The sensitivity and specificity of tests employing antigenic particles prepared by the technique of this invention are, as will be observed from Table 2, very high.

A special advantage of the techniques of this invention is the reproductibility and precision of tests which employ test reagents produced by the forced adsorption technique of this invention.

Results similar to those described above for *R. rickettsii* are observed with other rickettsia when similarly tested.

For example, sera from 155 *R. typhi* patients were tested by the forced adsorption slide latex agglutination test of this invention with the following results:

Sensitivity—93.8%
Specificity—99.1%

In addition to the high sensitivity and specificity, the tests of this invention offer the practical advantage of reducing workload; 5 College of American Pathologists (CAP) units for the latex test, as against 25 units for micro-IF, indirect hemagglutination or complement fixation tests.

The principal advantages of the procedures are described herein are:
1. Large amounts of high purity antibodies and antigens are not required.
2. High sensitivity.
3. High specificity.
4. Excellent reproductibility and precision of results utilizing test reagents from various sources.
5. Reduced workload for technicians.
6. Sophisticated equipment is not required.
7. Test can be conducted rapidly in the physician's office.

All of these advantages result in improved economy.

What is claimed is:

1. A process for the preparation of test reagents suitable for serological testing of mammalian sera for the presence of antigens or antibodies, said reagent comprising a test material of antigen or antibody adsorbed on the adsorbent surface of an adsorbent substrate which comprises preparing a solution containing dissolved test material in a solvent in the presence of an adsorbent substrate and adding to the solution an organic liquid precipitating reagent which is miscible with the solvent but does not dissolve the test material or the adsorbent substrate whereby the test material precipitates as an adsorbent on the surface of the adsorbent substrate.

2. A process for the preparation of test reagents for serological testing of mammalian sera for the presence of antigens or antibodies said reagent comprising a test material of antigen or antibody adsorbed on the adsorbent surface of an adsorbent substrate which comprises preparing in a container an aqueous solution said solution containing dissolved test material in the presence of the adsorbent substrate and adding to the solution a mixture of a water soluble alkali metal salt and a lower water soluble alcohol whereby the test material precipitates as an adsorbent on the adsorbent surface.

3. A process as in claim 2 wherein the adsorbent surface is the surface of a particle.

4. A process as in claim 2 wherein the adsorbent surface is the substantially flat surface of the container.

5. A process as in claim 2 wherein the adsorbent surface is the substantially flat surface of a polymer membrane supported in the aqueous solution when the mixture of alkali metal salt and alcohol is added.

6. A process for the preparation of tests reagents suitable for serological testing of mammalian sera for the presence of a rickettsial infection which comprises preparing an aqueous solution containing a dissolved rickettsia antigen and suspended adsorbent particles and adding to the solution a mixture of a water soluble alkali metal salt and a lower water soluble alcohol whereby the antigen precipitates in the adsorbent surface.

7. A process as in claim 6 wherein the adsorbent is a latex.

8. A process as in claim 7 wherein the rickettsia is *Rickettsia rickettsii;* the alkali metal salt is sodium acetate and the alcohol is ethanol.

9. A process as in claim 7 wherein the rickettsia is *Rickettsia prowazeki,* the alkali metal salt is sodium acetate and the alcohol is ethanol.

10. A process as in claim 7 wherein the rickettsia is *Rickettsia typhi,* the alkali metal salt is sodium acetate and the alcohol is ethanol.

11. A process for the preparation of test reagents suitable for serological testing of mammalian sera for the presence of rheumatoid arthritis antibodies which comprises preparing solution of Fraction II globulin containing a suspension of latex particles and adding to the solution a mixture of water soluble alkali metal salt and a water soluble alcohol whereby the Fraction II globulin precipitates on the adsorbent surface of the latex particles.

12. A process as in claim 11 wherein the salt is sodium acetate and the alcohol is ethanol.

13. A process for the preparation of test reagents suitable for serological testing of mammalian sera for the presence of *Escherichia coli* antibodies which comprises preparing a solution of dissolved lipopolysaccharide antigens from *Escherichia coli* containing a suspension of latex particles and adding to the solution a mixture of a water soluble alkali metal salt and a water soluble alcohol whereby the antigen precipitates on the adsorbent surface of the latex particles.

14. A process as in claim 13 wherein the salt is sodium acetate and the aclohol is ethanol.

15. A process for the preparation of test reagents suitable for serological testing of mammalian sera for the presence of trichinosis antibodies which comprises preparing a solution of dissolved trichinosis antigen containing a suspension of latex particles and adding to the solution a mixture of a water soluble alkali metal salt and a water soluble alcohol whereby the antigen precipitates on the adsorbent surface of the latex particles.

16. A process as in claim 15 wherein the salt is sodium acetate and the alcohol is ethanol.

17. A process for the preparation of test reagents suitable for serological testing of mammalian sera for the presence of toxoplasma antibodies which comprises preparing a solution of dissolved toxoplasma antigen containing a suspension of latex particles and adding to the solution a mixture of a water soluble alkali metal salt and a water soluble alcohol whereby the antigen precipitates on the adsorbent surface of the latex particles.

18. A process as in claim 17 wherein the salt is sodium acetate and the alcohol is ethanol.

19. A process for the preparation of test reagents suitable for serological testing of mammalian sera for the presence of chlamydial antibodies which comprises preparing a solution of dissolved chlamydial antigen containing a suspension of latex particles and adding to the solution a mixture of a water soluble alkali metal salt and a water soluble alcohol whereby the antigen precipitates on the adsorbent surface of the latex particles.

20. A process as in claim 19 wherein the salt is sodium acetate and the alcohol is ethanol.

* * * * *